United States Patent [19]
Pfanstiehl

[11] Patent Number: 6,055,860
[45] Date of Patent: May 2, 2000

[54] METHOD FOR MEASURING VEHICLE DAMAGE

[76] Inventor: John Pfanstiehl, 448 Harbor Dr. South, Indian Rocks Beach, Fla. 33785

[21] Appl. No.: 08/987,643

[22] Filed: Dec. 9, 1997

[51] Int. Cl.[7] .............................. G01N 9/24; G01B 17/02
[52] U.S. Cl. .................................. 73/600; 73/600; 73/627
[58] Field of Search ............................ 73/600, 627, 800, 73/801; 356/237.1–237.5; 33/174

[56] References Cited

U.S. PATENT DOCUMENTS

| | | |
|---|---|---|
| 3,855,943 | 12/1974 | Yagiela et al. . |
| 4,265,120 | 5/1981 | Morris et al. ............................ 73/600 |
| 4,507,872 | 4/1985 | Schermann . |
| 4,920,385 | 4/1990 | Clarke et al. ........................... 356/237 |
| 5,038,615 | 8/1991 | Trulson et al. . |
| 5,091,647 | 2/1992 | Carduner et al. . |
| 5,293,132 | 3/1994 | Koch . |
| 5,377,098 | 12/1994 | Sakai . |
| 5,436,726 | 7/1995 | Ventura et al. ......................... 356/371 |
| 5,449,864 | 9/1995 | Beatty et al. . |
| 5,463,464 | 10/1995 | Ladewski . |
| 5,572,324 | 11/1996 | Ventura .................................. 356/371 |
| 5,636,024 | 6/1997 | Crookham et al. ..................... 356/371 |

Primary Examiner—Harshad Patel
Assistant Examiner—Abdullahi Aw-Musse
Attorney, Agent, or Firm—Gifford, Krass, Groh, Sprinkle, Anderson & Citkowski, PC

[57] ABSTRACT

A method for producing objective, verifiable data which discovers and documents hidden prior vehicle paint and body damage by measuring paint with non-destructive instrumentation at several locations on the exterior surface of an automotive vehicle's body panels, comparing the highest and lowest of these measurements with the standard maximum and minimum measurements, and evaluating the vehicles as to the extent and location of repainting or body damage. Another step of calculating the range of the vehicle's measurements, and comparing these measurements and their range to the normal measurement variations found on new or unrepaired vehicles provides more conclusive evidence of repainting. A vehicle is then evaluated as having one or more body panels refinished if the range of measurements is greater than normal acceptable factory variation. The method also includes steps to further evaluate prior damage as excessively buffed paint, rust damage, minor collision damage, severe collision damage, sectioning, and switched VIN's on stolen cars. The paint measurements include thickness, surface finish and color.

29 Claims, 4 Drawing Sheets

METHOD FOR MEASURING VEHICLE DAMAGE

FIELD OF THE INVENTION

The present invention relates to the inspection and evaluation of mass produced vehicles through use of objective physical measurements of the vehicle's paint at numerous locations on the exterior surface of body panels. The inspection measurements are non-destructive and include coating thickness, surface finish, and color measurements made of the vehicle to be compared against other like vehicles or normal acceptable factory standards. The evaluation determines existence of original factory paint, refinish paint, excessively buffed paint, rust damage, collision damage, sectioning, and switched VIN's.

BACKGROUND OF THE INVENTION

The value of used vehicles is a major concern of wholesale buyers and sellers, insurers, and car owners. A principal determinant of the value of a vehicle is its damage history. The reliability of the mechanical and electronic components of both foreign and domestic vehicles has increased to the extent that the main concern of buyers of late model used cars is "Has this been in an accident?" And if the vehicle had collision damage, it is valuable to know if it was serious. Buyers want to know if the damage was confined to a parking lot ding on one body panel, damage to many panels, or perhaps worse, if the vehicle was "sectioned." A sectioned car is one which is fabricated by welding together the halves of two different severely damaged cars. Another serious concern of car buyers who live in coastal and rust belt areas is whether the vehicle's body has hidden rust damage. Whether the vehicle is stolen is now increasingly of concern, too. There is no prior objective, verifiable, and highly accurate method which can easily be used in the field to measure and evaluate both hidden paint and body damage on a vehicle.

It is known that application of paint on mass produced vehicles is one of the most expensive processes in their manufacture. Manufacturer's paint specifications, hereafter termed factory paint standards, include acceptable ranges for paint thickness, surface finish and color on vehicles leaving the factory.

Application of paint to vehicles after they leave the factory is termed "refinishing" and is performed to repair paint damage or as the final step in the repair of body damage. In contrast to manufacturers paint, the refinish industry has no strict, defined paint application specifications comparable to factory standards nor does the refinish industry have any standards which require measuring of these paint parameters. In fact it is rare to find a body shop which has instrumentation to measure surface finish, thickness, and color. Refinish work is almost universally judged by a subjective determination of "good enough" or "not good enough" by the body shop or the customer.

SUMMARY OF THE INVENTION

It is therefore an object of the invention to discover and evaluate hidden paint and body damage by the method of measuring certain paint parameters on the exterior body panels of a used vehicle and comparing them with the factory paint standards according to specific, objective, and well defined procedures. The methods of the present invention and the instruments utilized by these methods can be used by technicians in the field. The methods of the present invention were created for a relatively new generation of paint measurement instruments which are affordable and light weight. Additionally, the methods of the present invention do not require extensive technical training.

In the method of the present invention, a technician takes measurements of a given paint parameter at multiple locations on body panels of a vehicle. The highest measurement and the lowest measurement are identified and compared with the factory standard minimum and maximum values. These measurements are preferably taken with an electronic paint coating thickness gauge including circuitry for measuring both ferrous and non-ferrous surfaces. The gauge preferably measures surfaces in a non-destructive manner and employs sensors, such as an eddy current sensor and/or magnetic induction sensor. Another preferred gauge may have a sensor having a Hall effect with temperature sensor, or an ultrasonic sensor, it being understood that the gauge is not limited to any particular sensor.

If the vehicle's highest measurement is not higher than the factory standard maximum value and if the vehicle's lowest measurement is not lower than the factory standard value, than the vehicle can be evaluated as having no evidence of refinish or body work. For example, if the lowest vehicle coating thickness measurement is 4.5 mil and the highest is 5.5, and this is compared with a normal factory minimum paint thickness of 4.0 mils and a normal factory maximum paint thickness is 6.5 mils, the vehicle can be evaluated as having no evidence of refinish or body work.

Measurement of a particular vehicle's paint, identification of its lowest and highest measurements and comparison to maximum and minimum factory standards produces valuable information. For example, in the method of the present invention, if the lowest thickness measurement is less than the minimum factory standard, then the paint on that panel can be evaluated as over-buffed. If the highest thickness measurement is greater than the maximum factory standard, then the paint on that panel can be evaluated as refinished.

Determination of refinished panels is extremely valuable because repairs of collision and rust damage are hidden by refinish work. Because discovery of refinished panels is vital to the discovery of serious hidden damage, the method of the present invention has an additional step to enable further precision in the detection of refinish work. After refinished panels are identified, the method of the present invention inspects them further to determine whether hidden damage exists and further identifies it as rust damage, minor collision damage, serious collision damage known as "sectioning" or the switched VIN of a stolen vehicle.

BRIEF DESCRIPTION OF THE DRAWINGS

The present invention will be more fully understood by reference to the following detailed description of the preferred embodiments of the present invention when read in conjunction with the accompanying drawing, in which like reference characters refer to like parts throughout the views, and in which.

DETAILED DESCRIPTION OF THE PREFERRED EMBODIMENTS OF THE PRESENT INVENTION

Before beginning the inspection of the paint on a vehicle, the technician should test the calibration of the inspection instruments. The methods for checking calibration are described in the instruction manuals supplied by the instrument manufacturers and while they vary in their steps, they generally involve taking a measurement on reference standards. In practice, the technician will soon learn whether individual instruments need their calibration checked once per car, once per day, or once per week or month.

The technician should begin taking readings on the end of the car which is most likely to have damage: the front end. In particular, the hood is a good starting place because it is primarily a horizontal surface and therefore is more likely to have suffered environmental damage from acid rain and ultraviolet light than the primarily vertical surfaces of fenders or doors. The reason for inspecting the most likely area of damage first is to save time. For example, a car buyer may be looking for an entirely undamaged car and therefore the purpose of that inspection is solely to determine if any level of damage exists. If any is found, the inspection can stop. The reason for the inspection can make another starting point a better choice. For example, an inspector solely looking for stolen cars should check the Vehicle Identification Number or VIN first.

For most inspections, the paint is inspected starting with the hood, then moving to the roof, and the trunk. The horizontal surfaces are generally inspected first since they are more likely to have suffered damage from environment pressures such as UV light and falling chemicals. In addition, many makes of vehicles have different specification for paint thickness and gloss on horizontal panels than on vertical panels. Inspecting all the horizontal panels first makes it easier to detect any variation from panel to panel.

The number of inspection points per panel is set according to the likelihood of problems. For example, it is valuable to have more readings on the hood than on the roof. The hood has the same environmental pressures as the roof but has the added pressure of the engine heat and a far greater likelihood of collision damage than the roof.

The inspection should progress from the same starting point and in the same pattern each time to make the inspection process habitual, allowing the technician to concentrate on the value of the paint readings.

The first goal of the inspection is to discover any refinish work. Refinish work alone cannot only devaluate a vehicle but also acts as a red flag to the possibility of hidden collision or rust damage. After refinish paint work is discovered, those refinished panels can be examined much more closely to determine if hidden body damage exists. Examining every panel of the body this closely is a practical impossibility in most applications, and therefore discovering refinish work is the key to efficiently discovering hidden body damage.

The method of the present invention is comprised of two separate means of discovering refinish work. The first method involves examining the absolute value of the vehicle's paint measurement and comparing it to the standard minimums and maximums found generally on factory finished vehicles regardless of the plant the vehicle is produced at or the color or method of paint application for that type of vehicle. The second preferred method involves ascertaining the range of highest and lowest measurements on a vehicle and comparing this range to standard minimums and maximums found on factory finished vehicles having the same paint system and paint color. Obviously, this method is more precise.

Figure 1:
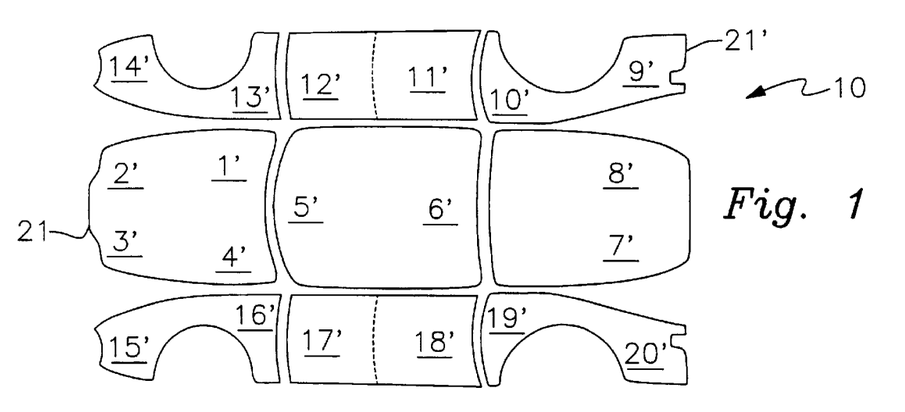
FIG. 1 is a top plan view of a vehicle's body panels.

The following descriptions of the first method will utilize paint thickness measurements, although the method also works with color measurement and surface finish measurement. FIG. 1 is a representation of the exterior panels on a vehicle 10. The series of reference numerals 1'–20' indicate one pattern which can be used to follow around a vehicle 10 to take paint measurements in a systematic pattern. In the sample measurement pattern of FIG. 1, a larger number of readings are taken on panels which are more likely or more important indicators of damaged areas.

In the following description of the method of the present invention, the standard minimum and maximum paint thickness measurement found on factory finished vehicles are 4.0 mils and 6.5 mils respectively. If the lowest and highest measurements taken along a pattern on the vehicle, such as that shown in FIG. 1, were 4.5 mils and 5.5 mils respectively, the vehicle 10 is evaluated as having no evidence of refinish work at this stage. If, however, the measurements on the hood panel 21, corresponding to locations 1', 2', 3', 4' in FIG. 1, are less than 4.0 mil, panel 21 is evaluated has having thin or overly-buffed paint. In other words sanding or buffing has removed paint from panel 21 to the extent that it is less than standard minimum thickness. Furthermore, if the lowest paint thickness readings of panel 21 are less than 3.5 mils, the panel is evaluated as having severely thin over-buffed paint because the measurements are in excess of 0.5 mils under the standard minimum thickness.

If measurements taken on the left rear quarter panel 21' of the vehicle 10, locations 9' and 10' in FIG. 1, are higher than the 6.5 mil normal factory maximum, then quarter panel 21' is evaluated as having been refinished.

The quarter panel 21' evaluated as "refinished" is then examined more closely to discover if hidden body damage exhibited by use of body filler exists under the refinish paint. The additional body filler locating measurements are taken in a systematic pattern across the fall exterior surface of the refinished panel.

Figure 2:
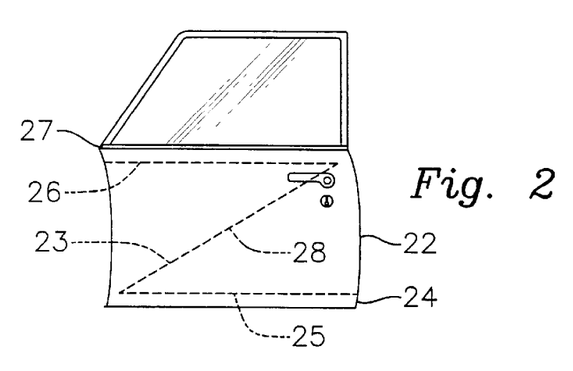
FIG. 2 is a side view of a vehicle body panel with Z test measurement.

With reference to FIG. 2, a body panel 22 is shown for measurement. The technician takes measurements generally along a specified pattern including lines from one corner 27 of the panel 22 to another 24 and preferably including measurements taken about the center 28 of the panel 22. FIG. 2 shows lines of measurement in a "Z" pattern 27 although other patterns such as an "X" pattern, and "O" pattern or parallel lines can suit other applications.

The Z pattern suits panels where damage is most likely to occur along the borders 25, 26 of the panel 22 covered by the parallel lines of the Z. For example on a door panel 22, the upper line 26 of measurements extends along the top 27 of the door, which is a likely area for rust damage in vehicles in coastal regions of a country. Measurements continue through the center 28' along line 23 and the lower line 25 of the Z extending along the lower lip 24 of the door, which is a likely area for rust damage in rust-prone regions of a country. If thickness measurements are greater than 10 mils above the standard maximum thickness measurement, then that location is evaluated as a location of body filler. Common coating thickness gauges cannot differentiate between the paint coating on the surface and the underlying body filler coating. In practice, however it is rare that refinish paint thickness exceeds 10 mils above standard maximum thickness and therefore thickness in excess of 10 mils is evaluated as a location of body filler.

Figure 3:
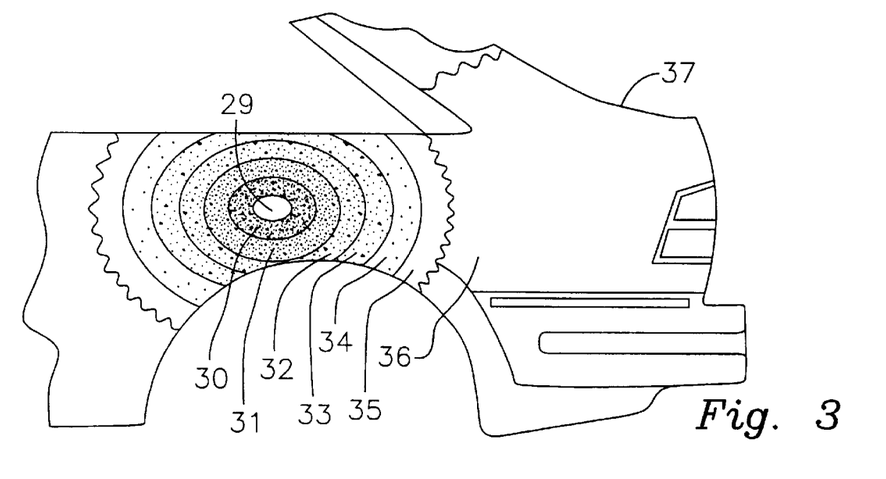
FIG. 3 is a cutaway side view of a vehicle body panel showing an example of feather edging.

As shown in FIG. 3, although rust perforation dents may cover only a small portion 29 of the area of the body panel 37, their repairs are "feather-edged" 30, 31, 32, 33, 34, 35 to blend the body filler and refinish paint into the surrounding panel. Paint measurements taken in the area of feathering or blending will provide evidence of repairs. By this means, the systematic pattern of thickness measurements efficiently enables the method of this invention to discover areas of damage without the prohibitively time-consuming process of taking measurements on every square inch of the panel.

Figure 4:
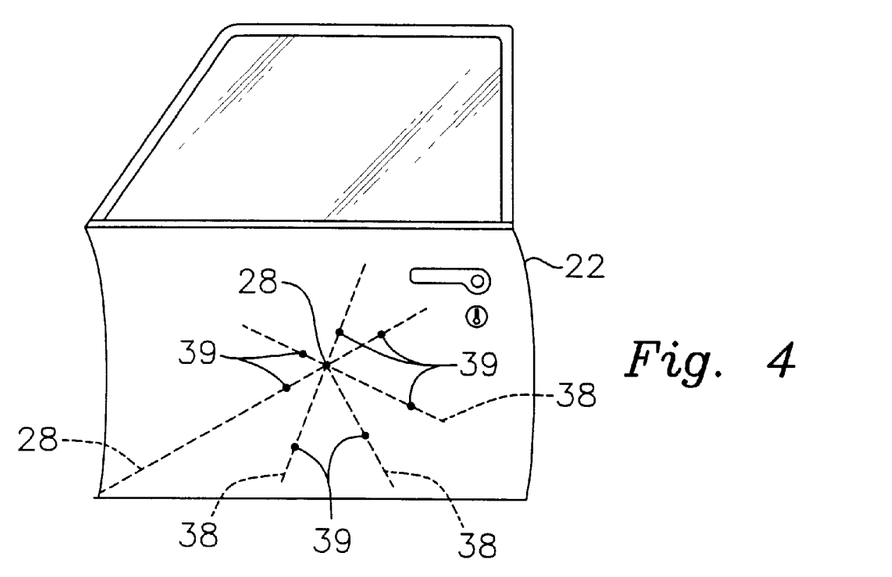
FIG. 4 is a side view of a vehicle body panel showing mapping of measurements.

With reference to FIGS. 3 and 4, when a location of body filler 29 is discovered the surrounding area of the panel 36 is more closely examined to determine the extent of the hidden damage. Additional measurements preferably are taken along four or more lines extending out radially from the location of body filler 29. FIG. 4 shows a body panel with radial measurement lines 28, 38 passing through the center 28' of the body panel 22. The points 39 at which the thickness measurement drops below 10 mils plus the standard maximum thickness is evaluated as the border of the hidden rust or collision damage. The area within the border is evaluated as hidden rust or collision damage.

The hidden rust or collision damage is further evaluated based on the radial line measurements shown in FIG. 3 at 30, 31, 32, 33, 34, 35. If the total area of hidden damage, 30, 31, 32, 33, 34 and 35 is less than six inches wide and no coating measurement is greater than 40 mils, the area is evaluated as minor damage.

Figure 5:
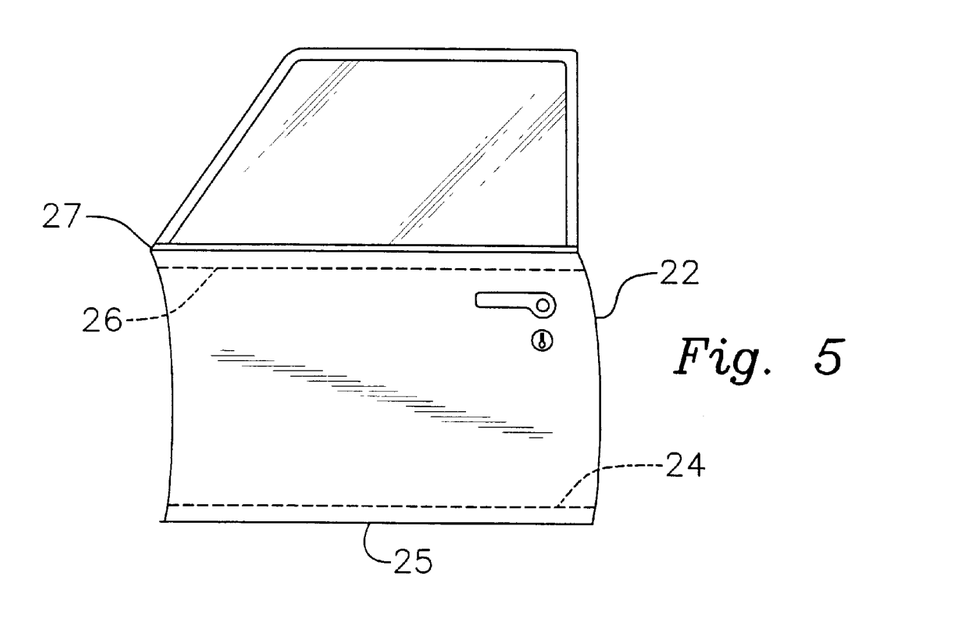
FIG. 5 is a side view of a vehicle door showing rust prone areas.

The method of the present invention has additional rust damage locating measurements on vehicles over three years old. The measurements are taken on areas which are most likely to have rust damage. These areas are different depending on the region of a country the vehicle is from. With reference to FIG. 5, in rust-belt regions, rust damage locating measurements are taken on the areas 26 near the lower edge 25 of doors 22, fenders and rear quarter panels. In coastal regions, measurements are taken on areas 26 near edges 27 of body panel 22 abutting the vehicle's door glass, and windshields, and body panel edges on trunks and hoods abutting moldings. Measurements greater than 10 mils above standard maximum thickness measurements are evaluated as location of hidden rust damage.

Figure 6:
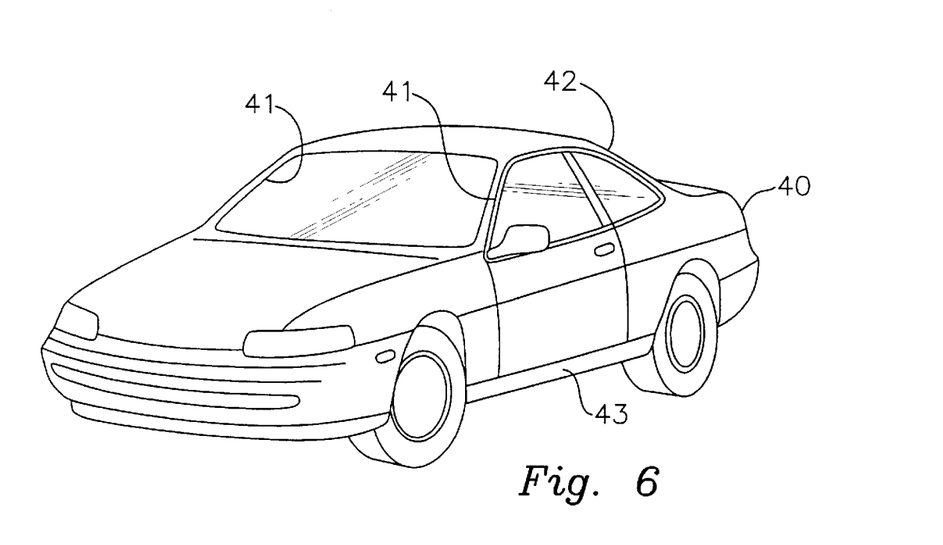
FIG. 6 is a perspective view of a vehicle body shown sectioning.

With reference to FIG. 6, the method of the present invention includes additional sectioning locating measurements of a vehicle 40 taken on windshield posts 41, sail panels 42 and rocker panels 43. These are the areas where severely crashed cars are cut in half. The least badly damaged halves of two different cars are welded together to salvage one composite vehicle. Measurements greater than 10 mils above standard maximum thickness measurements are evaluated as location of severe collision damage, sectioning.

Figure 7:
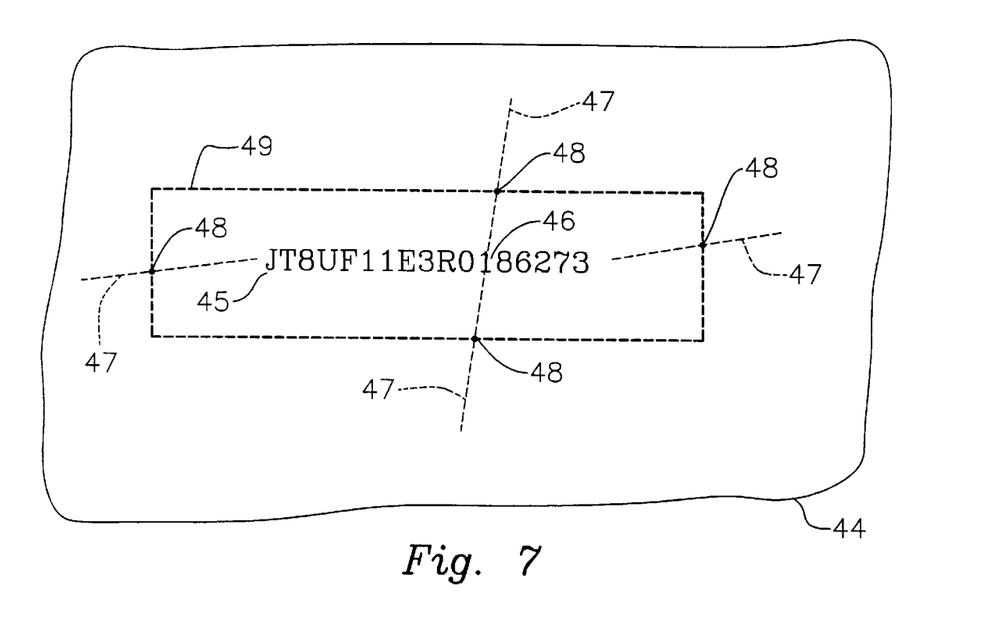
FIG. 7 is a cutaway front view of VIN panel located on a vehicle body.

The method of the present invention has additional measurements taken of the plate 49 comprising Vehicle Identification Numbers, VIN, characters 45 in FIG. 7, and in radial lines 47 extending out from the characters 45. It has long been common practice for thieves to buy burnt or severely damaged vehicles to obtain their titles and then cut the VIN from the firewall or frame. A good condition vehicle of the same model is stolen, its VIN cut out and the other VIN welded in its place. The welds are ground down and a small amount of body filler 48 is used to hide grinding marks, low spots, and pits. The surrounding area is refinished and the vehicle is sold with the switched VIN. The factory paint on areas surrounding VIN's is very consistent and cosmetic refinishing on these areas is rarely done. The method of the present invention evaluates radial line measurements greater than 3 mils above the VIN character thickness measurements as having a switched VIN and thereby being stolen.

Because discovery of refinished panels is vital to the discovery of serious hidden damage, the method of the present invention has an additional step to enable further precision in the detection of refinish work. This second method calculates the range between the highest and lowest measurements found on the vehicle, the intra-vehicle variation, and compares this range to normal intra-vehicle factory paint variation. If the range of intra-vehicle measurements is greater than normal intra-vehicle paint variation, then that vehicle is evaluated as having refinished panels.

Although each factory has a close tolerance for paint parameters, because of the wide differences in the type of application equipment and the type of paint systems from factory to factory, those paint parameters vary considerably between different makes of vehicles. For example, a plant applying a monocoat paint system may have a normal factory standard value for coating thickness of 4.0 to 5.5 mils. Another plant applying a clearcoat-basecoat paint system could have a factory standard value for paint thickness of 5.0 to 6.5 mils.

In any one plant, further variation can exist between different colors. In basecoat-clearcoat paint systems considerable variation exists in the thickness of the basecoat for different colors. The variations due to different plants, different makes, different colors and different paint systems add up to produce a relatively large range between the minimum factory standard and the maximum factory standards across the spectrum of models produced today.

In the preceding example of normal paint variation between two plants, measurement of paint parameters over the surface of one vehicle from either plant fall within a tighter range than measurements taken on vehicles from different plants, i.e. the range relied on in the first preferred method. In both plants in the example, the normal intra-vehicle thickness variation is less then 1.5 mil. If a vehicle's coating thickness measurements are all close to 4.0 mils except a right front fender which measures 6.0 mils, that vehicle's thickness range is 2.0 mils. When this is compared with the normal intra-vehicle thickness variation of 1.5 mil as set forth above, and found to exceed it, the vehicle is evaluated as having one or more panels damaged or refinished.

The steps detailed earlier in the description of the first preferred method of the present invention compared the lowest measurement and the highest measurement with the standard maximum and minimum thickness. Because the standard maximum and minimum thickness for vehicles has a greater range due to the many different plants vehicles come from, it is not as precise a screening method for discovering repaint as is the additional step of calculating the intra-vehicle thickness range and comparing that to normal intra-vehicle factory variation.

A finer degree of precision in screening for body filler locations and multiple refinishing is also enabled by examining intra-vehicle variation. Panels with coating thickness measurement over 2 mils higher than adjoining panels can be evaluated as having refinish work. The qualification that the thickness on the panel evaluated as "refinished" must also be greater than 5.5 mils, the normal maximum factory standard value, eliminates the possibility of a false evaluation caused by thin paint on over-buffed panels.

Evaluation of panels as "refinished" by means of intra-vehicle variation enables the evaluation of body filler locating measurement as "locations of body filler" when these measurements are 10 mils above the median highest thickness measurements used to calculate the intra-vehicle range.

The evaluation that a vehicle has "multiple refinishing" is made if the range of paint thickness variation is greater than 3 mils above the normal intra-vehicle factory variation.

The method of the present invention has been described using the measurement of coating thickness for clarity. The measurement of surface finish and paint color can also be used to discover and evaluate refinish work and hidden body damage by comparing lowest and highest readings established by the preferred methods described above and shown in FIGS. 1–5 with standard maximum and minimum measurements and by comparing intra-vehicle measurement range with normal factory intra-vehicle variation.

The paint parameters of color and surface finish can be judged visually with varying degrees of success by various painters without instrumentation and therefore it is possible for a good painter to produce refinish work whose color and surface finish fall within factory standard values. However, it takes considerable skill and additional work to make the surface finish of refinish painting closely match the "orange peel" of a factory applied finish. Painters seldom even try to exactly match factory surface finish because customers tend to perceive only the color match and level of gloss. Coating thickness cannot be seen by painters or customers and it is exceedingly difficult to match the factory standards for consistency of thickness when refinishing a vehicle. Therefore, at the present level of technology, surface finish is a more reliable indicator of refinish work than color, and coating thickness is the most reliable indicator of the three.

Figure 8:
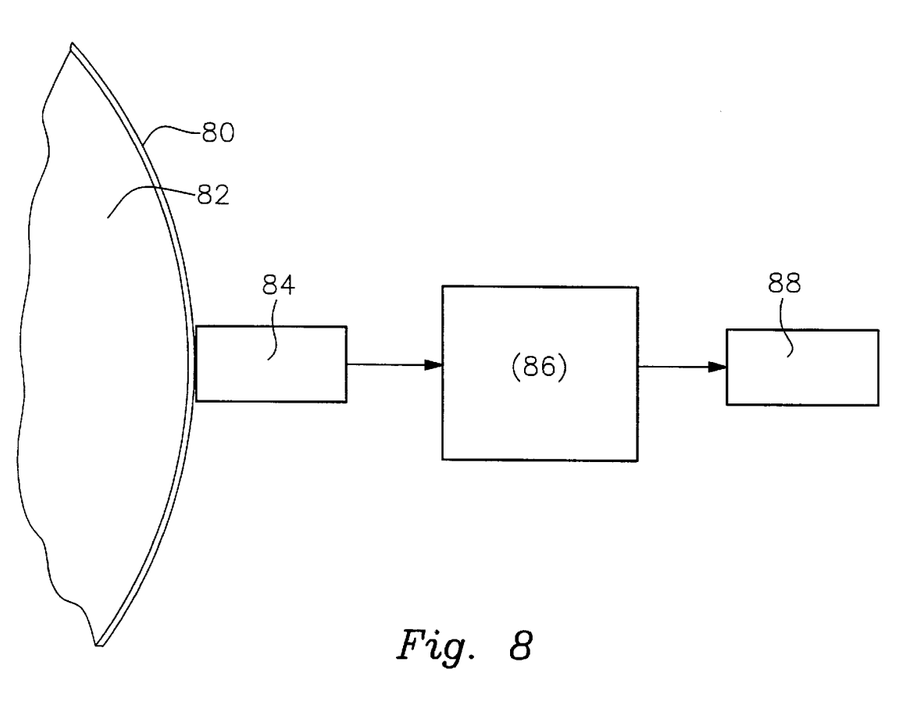
FIG. 8 is a simplified block diagram illustrating the way in which a sensor is interfaced to a gauge outputting a thickness measurement according to the invention.

FIG. 8 is a simplified block diagram illustrating the way in which a sensor 84 is used to sense the thickness of a coating 80 applied to the surface of a vehicle 82. The sensor 84 is interfaced to a gauge 86, which, in turn, outputs a thickness measurement identified by block 88. The gauge is not limited to any particular sensor, and may be analog or digital in nature based upon eddy-current and/or magnetic induction, Hall-effect, temperature or ultrasonic technology.

Having described my invention, however, many modifications thereto will become apparent to those skilled in the art to which it pertains without deviation from the spirit of the invention as defined by the scope of the appended claims.

I claim:

1. A method of gathering objective, verifiable data to discover, evaluate and document hidden, prior, or non-visible vehicle paint and body damage, said method comprising the steps of:

measuring the thickness of said vehicle paint with non-destructive instrumentation at several locations in a systematic pattern on the exterior surface of said vehicle body panels on a vehicle;

recording said paint thickness measurements;

identifying the highest and lowest of said measurements to determine the thickest and thinnest areas of paint coverage;

comparing said highest and lowest measurements respectively to standard maximum and minimum paint measurements found on known, undamaged like vehicles; and evaluating said vehicle as having a body panel damaged if said highest measurement is higher then said standard maximum measurement or it said lowest measurement is less than said standard minimum measurement.

2. The method of claim 1 wherein said non-destructive instrumentation measures the surface finish of said paint on said vehicle panels.

3. The method of claim 1 wherein said non-destructive instrumentation measures the color characteristics of light reflected off the surface of said paint on said vehicle panels.

4. The method of claim 1 wherein said non-destructive instrumentation measures the thickness of said paint and non-paint coatings on said vehicle and said vehicles panels using electronic analog and digital circuits with transducer input.

5. The method of claim 1 wherein said standard maximum and minimum paint measurements are the maximum and minimum measurements on said like vehicle at the time said vehicle leaves the factory.

6. The method of claim 4 wherein said vehicle paint and body damage is evaluated as having overly buffed paint if the lowest thickness measurement is less than said standard minimum thickness measurement.

7. The method of claim 4 wherein said vehicle paint and body damage is evaluated as having severely over-buffed paint if the lowest thickness measurement is more than one half mil less than said standard minimum thickness measurement.

8. The method of claim 5 wherein said vehicle paint and body damage is evaluated as having refinish work if the highest thickness measurement is greater than said standard maximum thickness measurement.

9. The method of claim 8 wherein said vehicle panels having coating thickness measurements greater than said maximum standard thickness measurements are evaluated as refinished body panels.

10. The method of claim 9 further comprising the step of:

taking additional measurements on said refinished body panels;

wherein said measurements are taken in a systematic pattern across the exterior surface of said refinished body panels.

11. The method of claim 10 wherein said additional measurements are evaluated as locations of body filler if said measurement is greater than 10 mils above said standard maximum thickness measurement.

12. The method of claim 11 comprising the additional step of:

measuring said paint thickness in four or more radial lines extending out from said body filler locations until said paint thickness measurement decreases to less than 10 mils above said standard maximum thickness measurement.

13. The method of claim 12 wherein the area bordered by measurements over 15 mils is evaluated as hidden rust or collision damage.

14. The method of claim 13 comprising the additional step of:

evaluating said hidden rust or collision damage area as being minor damage if said area bordered by measurements over 15 mils is less than six inches wide and wherein none of said body filler locating measurements is greater than 40 mils.

15. The method of claim 5 comprising the additional step of:

taking additional measurements on said vehicle panels where said vehicle is greater than three years old; said additional measurements taken in rust prone areas of said vehicle panels comprising the top and bottom front fenders and doors, bottom of rear fenders and rocker panels, painted surfaces near the bottom of the windshields, near front edge of hood and rear edge of trunk lid.

16. The method of claim 15 wherein measurements over 15 mils greater than the minimum coating thickness measurements are evaluated as being hidden rust damage.

17. The method of claim 4 comprising the additional steps of:

taking additional measurements on said vehicle in areas commonly used for sectioning the body halves of two separate cars together thereby creating a sectioned vehicle to repair severe collision damage, said areas comprising the windshield posts, sail panels and rocker panels of said vehicle.

18. The method of claim 17 wherein said measurements in excess of 10 mils greater than standard thickness measurements are evaluated as being severe hidden collision damage on said sectioned vehicle, said standard thickness measurements defined as the maximum measurement measured on said like vehicle on that area of that model and year of said like vehicle.

19. A method of gathering objective, verifiable data to discover, evaluate and document the vehicle paint and vehicle body damage, the method comprising the steps of:

measuring vehicle paint and non-paint coatings with non-destructive instrumentation at several locations on the exterior surface of said vehicle body panels using an electronic analog or digital transducer;

recording said measurements;

identifying the highest and lowest of said measurements;

comparing said highest and lowest measurements respectively to the standard maximum and minimum paint measurements associated with known undamaged like vehicles;

evaluating said vehicle as having a body panel damaged or refinished if said highest measurement is higher than said standard maximum measurement, or if said lowest measurement is less than said standard minimum measurement;

wherein at least certain of said measurements are taken between the characters on Vehicle Identification Numbers (VIN) stamped into metal panels on said vehicle; and additional measurements are taken along a radial line extending outwardly from said VIN.

20. The method of claim 19 wherein said vehicles having said radial line measurements being greater than 2 mils thicker than said thickness measurements on said VIN characters are evaluated as having a switched VIN and thereby being stolen.

21. A method of gathering objective, verifiable data to discover, evaluate and document hidden, prior, or non-visible vehicle paint and body damage, the method comprising the steps of:

measuring the thickness of said vehicle paint with non-destructive instrumentation at several locations in a systematic pattern on the exterior surface of said vehicle body panels;

recording said paint thickness measurements;

identifying the highest and lowest of said measurements to determine the thickest and thinnest areas of paint coverage;

calculating the difference between said highest and said lowest of said measurements to determine the range of said measurements on said vehicle;

comparing said range of said measurements on said vehicle with normal, acceptable factory variations; and evaluating said vehicle as having one or more of said vehicle body panels damaged or refinished if said range of said measurements is greater than said normal, acceptable factory variations.

22. The method of claim 21 wherein said non-destructive instrumentation measures the surface finish of said paint on said vehicle panels.

23. The method of claim 21 wherein said non-destructive instrumentation measures the color characteristics of light reflected off the surface of said paint on said vehicle panels.

24. The method of claim 21 wherein said non-destructive instrumentation measures the thickness of said paint and said vehicle panels using electronic analog and digital circuits with transducer input.

25. The method of claim 21 wherein said normal acceptable factory variation is the range of paint measurements on one like vehicle at the time it leaves the factory.

26. The method of claim 24 wherein said panels with said thickness readings which are greater than 5.5 mils and over two mils higher than the average of said thickness readings on other panels of said vehicle are evaluated as being refinished panels.

27. The method of claim 26 further comprising the steps of:

taking additional measurements on said refinished body panels;

said additional measurements being taken in a systematic pattern across the full exterior surface of said body panels;

evaluating said measurements as locations of body filler if said measurement is greater than 10 mils above said average thickness measurement.

28. The method of claim 24 wherein said vehicle is evaluated as having multiple refinishing if said range of paint thickness measurements is greater than 3 mils over said normal acceptable factory variation.

29. A method for producing objective, verifiable data which discovers, evaluates and documents vehicle paint and vehicle body damage comprising:

measuring said vehicle paint with non-destructive instrumentation at several locations on the exterior surface of said vehicle body panels;

recording said measurements;

identifying the highest and lowest of said measurements;

comparing said highest and lowest measurements respectively to the standard maximum and minimum paint measurements found on known undamaged like vehicles;

evaluating said vehicle as having a body panel damaged or refinished if said highest measurement is higher than said standard maximum measurement or if said lowest measurement is less than said standard minimum measurement;

wherein said standard maximum and minimum paint measurements are the maximum and minimum measurements on said like vehicle at the time said vehicle leaves the factory;

wherein said vehicle paint and body damage is evaluated as having refinish work if the highest thickness measurement is greater than said standard maximum thickness measurement;

wherein said vehicle panels having coating thickness measurements greater than said maximum standard thickness measurements are evaluated as refinished body panels; and further comprising the step of:

taking additional measurements on said refinished body panels;

wherein said measurements are taken in a systematic pattern across the exterior surface of said refinished body panels.

* * * * *